(12) United States Patent
Bui

(10) Patent No.: US 10,525,156 B1
(45) Date of Patent: Jan. 7, 2020

(54) METHOD OF USING A GASTRO-INTESTINAL SCOPE FOR THE DISINFECTION OF A COLON

(71) Applicant: Phong Duy Bui, San Diego, CA (US)

(72) Inventor: Phong Duy Bui, San Diego, CA (US)

( * ) Notice: Subject to any disclaimer, the term of this patent is extended or adjusted under 35 U.S.C. 154(b) by 0 days.

(21) Appl. No.: 16/258,078

(22) Filed: Jan. 25, 2019

Related U.S. Application Data

(63) Continuation-in-part of application No. 16/053,930, filed on Aug. 3, 2018, now Pat. No. 10,188,483.

(51) Int. Cl.
| | | |
|---|---|---|
| *G01N 21/00* | (2006.01) | |
| *A61N 5/00* | (2006.01) | |
| *A61L 2/00* | (2006.01) | |
| *A61B 1/00* | (2006.01) | |
| *A61B 1/12* | (2006.01) | |
| *A61L 2/10* | (2006.01) | |
| *A61M 39/16* | (2006.01) | |
| *A61M 25/01* | (2006.01) | |
| *A61B 1/012* | (2006.01) | |
| *A61M 25/00* | (2006.01) | |
| *A61M 39/02* | (2006.01) | |

(52) U.S. Cl.
CPC .......... *A61L 2/10* (2013.01); *A61M 25/0108* (2013.01); *A61M 39/16* (2013.01); *A61B 1/012* (2013.01); *A61M 25/0097* (2013.01); *A61M 39/02* (2013.01); *A61M 2039/167* (2013.01); *A61M 2210/1064* (2013.01)

(58) Field of Classification Search
CPC ....................................................... A61L 2/10

USPC .......... 422/24; 600/101, 133, 136, 153, 155, 600/157, 523; 250/455.11, 494.1, 492.1, 250/435
See application file for complete search history.

(56) References Cited

U.S. PATENT DOCUMENTS

| | | |
|---|---|---|
| 4,862,872 A | 9/1989 | Yabe et al. |
| 5,240,675 A | 8/1993 | Wilk et al. |
| 5,637,877 A | 6/1997 | Sinofsky |
| 7,399,273 B2 | 7/2008 | Moriyama et al. |
| 7,887,640 B2 | 2/2011 | Kawai et al. |
| 7,905,831 B2 | 3/2011 | Noguchi et al. |
| RE43,281 E | 3/2012 | Higuma et al. |
| 8,979,738 B2 | 3/2015 | Hsu et al. |
| 2007/0176117 A1 | 8/2007 | Redmond et al. |
| 2010/0191049 A1 | 7/2010 | Mandava et al. |
| 2012/0035527 A1* | 2/2012 | Tearney ............... A61L 27/3604 604/20 |
| 2015/0165185 A1* | 6/2015 | Cohen ........................ A61L 2/10 128/207.14 |
| 2016/0114185 A1* | 4/2016 | Mankin ................ A61N 5/0624 607/92 |
| 2017/0119915 A1 | 5/2017 | Lin et al. |

* cited by examiner

*Primary Examiner* — Monzer R Chorbaji
(74) *Attorney, Agent, or Firm* — James R. McDaniel

(57) ABSTRACT

A gastro-intestinal (GI) scope device for use in the disinfection of a patient's colon including a gastro-intestinal (GI) scope having an insertion tube and a universal cord, an ultraviolet (UV) light assembly, and a UV light sleeve assembly, wherein the UV light assembly includes a power source, a UV light box operatively connected to the power source, and a UV light source operatively connected to the UV light box, wherein the UV light source is located within an interior of the insertion tube and the UV light sleeve assembly is located on an end of the insertion tube in order to disinfect a patient's colon.

17 Claims, 7 Drawing Sheets

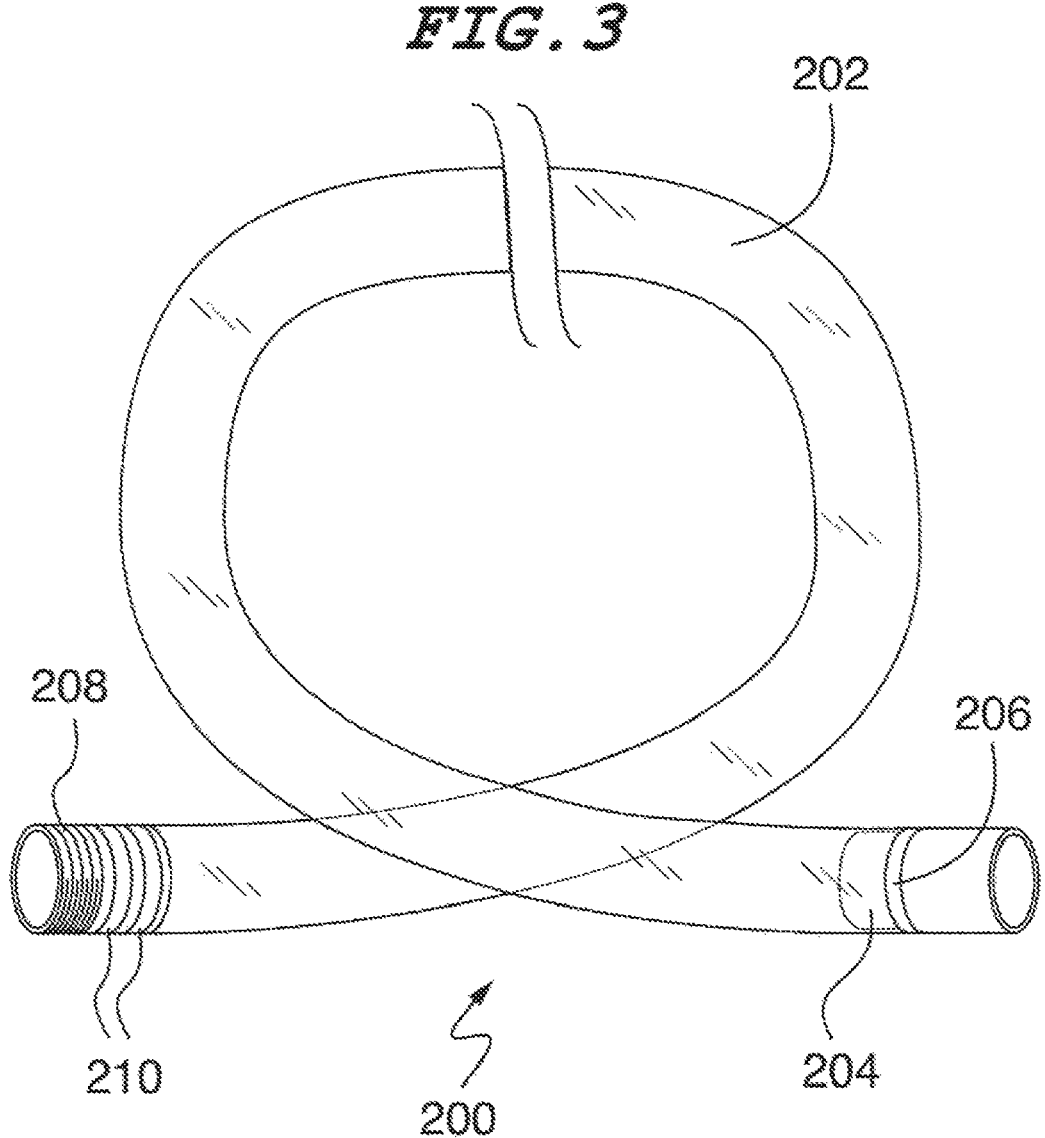

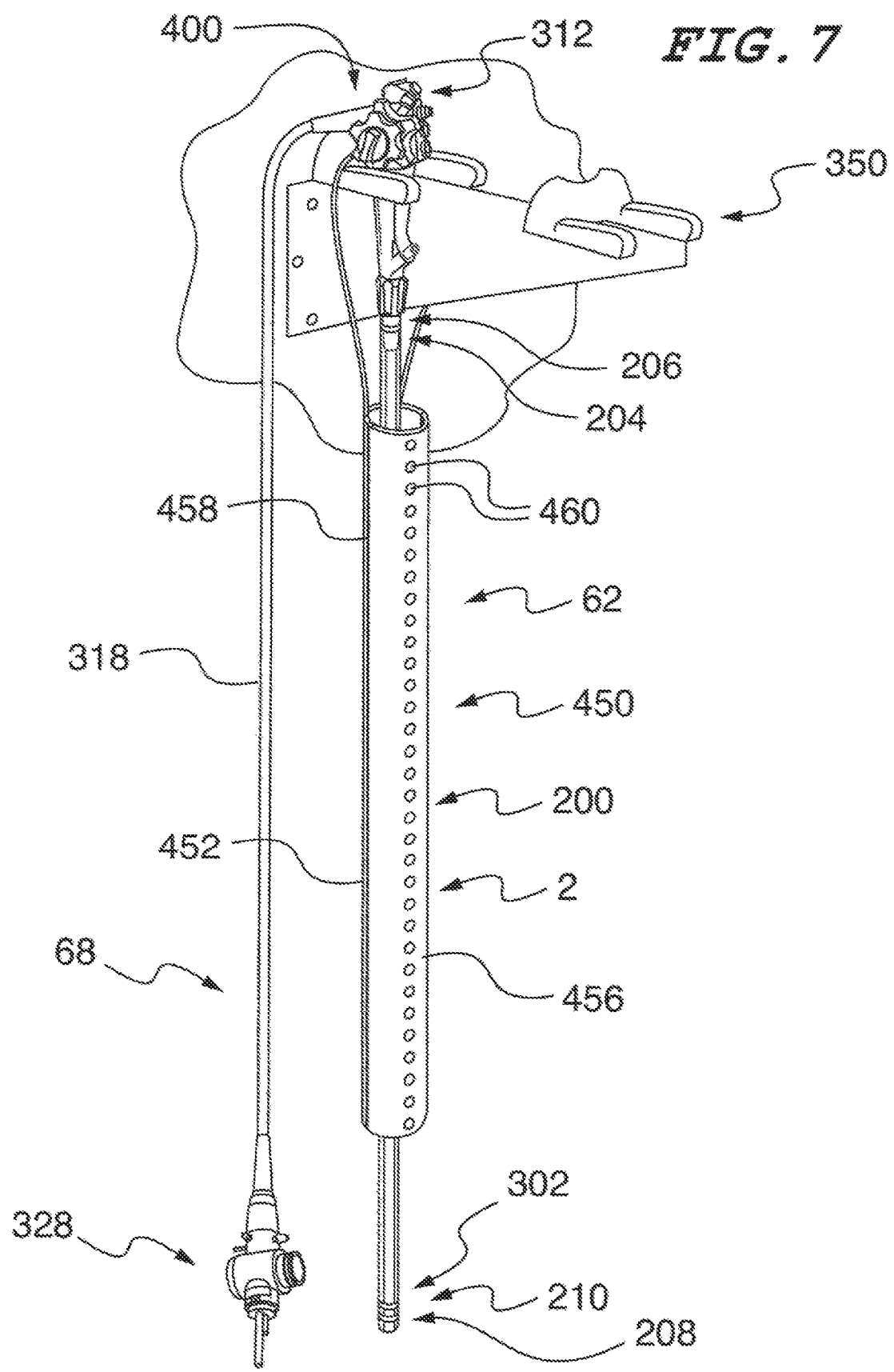

METHOD OF USING A GASTRO-INTESTINAL SCOPE FOR THE DISINFECTION OF A COLON

CROSS-REFERENCE TO RELATED APPLICATION

This application is a continuation-in-part of U.S. patent application Ser. No. 16/053,930, filed on Aug. 3, 2018, the disclosure of which is hereby incorporated by reference in its entirety to provide continuity of disclosure to the extent such a disclosure is not inconsistent with the disclosure herein.

FIELD OF THE INVENTION

The present invention is generally related to a programmable device that can be used in conjunction with a gastro-intestinal (GI) scope, wherein the device is used during a colonoscopy by utilizing UV light to eradicate clostridium difficile (C. Diff) in infected patients and can also be used to eradicate a multitude of other bacteria by utilizing a programmable ultraviolet (UV) light source which is connected to fiber optic cords, wherein the fiber optic cords fit inside of the GI scope lumen for the purposes of disinfecting and sterilizing the interior of the colon. In this manner, the programmable UV light source will be able to disinfect the colon and possibly provide sterilization of the colon. Also, the programmable UV light source may be able to be programmed to provide the desired disinfection and sterilization.

BACKGROUND OF THE INVENTION

Prior to the present invention, as set forth in general terms above and more specifically below, it is known, to employ various types of liquid or chemical systems to disinfect GI scopes. Furthermore, it is known that GI scopes must be cleaned every seven days even if the GI scope has not been used. See for example, U.S. Pat. No. 4,862,872 by Yabe et al., U.S. Pat. No. 5,240,675 by Wilk et al., U.S. Pat. No. 7,399,273 by Moriyama et al., U.S. Pat. No. 7,887,640 by Kawai et al., U.S. Pat. No. 7,905,831 by Noguchi et al., U.S. Pat. No. 8,979,738 by Hsu et al., U.S. Pat. RE43,281 by Higuma et al., and U.S. Patent Application 2017/0119915 by Lin et al. While these various liquid or chemical systems for disinfecting GI scopes may have been generally satisfactory, there is nevertheless a need for a new and improved programmable device that can be used in conjunction with a gastro-intestinal (GI) scope, wherein the device is capable of disinfecting and sterilizing the GI scope by utilizing a programmable ultraviolet (UV) light source.

It is a purpose of this invention to fulfill these and other needs in the GI scope disinfecting and sterilizing art in a manner more apparent to the skilled artisan once given the following disclosure.

BRIEF SUMMARY OF THE INVENTION

A first aspect of the present invention is a method of using a gastro-intestinal (GI) scope for the eradication of clostridium difficile (C. Diff) in a patient's colon, including the steps of: providing a gastro-intestinal (GI) scope having an insertion tube having a first end and a second end, a control section such that the second end of the insertion tube is operatively connected to the control section, a universal cord having a first end and a second end such that the first end of the universal cord is operatively connected to the control section and the second end of the insertion tube is operatively connected to a suction connector providing an ultraviolet (UV) light assembly, wherein the UV light assembly is further comprised of; a power source, a first electrical extension operatively connected to the power source, a UV light box operatively connected to the first electrical extension, and a UV light source operatively connected to the UV light box, wherein the UV light source includes a first end and a second end and wherein the UV light source is further comprised of a UV light having a tube and a plurality of UV lights located on the tube; inserting the insertion tube into a patient's colon such that the first end of the insertion tube is located adjacent to a cecum of the patient's colon; inserting the UV light source into the insertion tube until the first end of the UV light source is located adjacent to the first end of the insertion tube and the cecum of the patient's colon; and removing the insertion tube and the UV light source from the patient's colon while simultaneously activating the UV light source in order to eradicate clostridium difficile (C. Diff) located in a patient's colon.

In one embodiment of the first aspect of the present invention, the step of providing an ultraviolet (UV) light assembly further includes the step of providing UV light source extension such that the UV light source extension is operatively connected to the UV light box and the UV light source.

In another embodiment of the first aspect of the present invention, the method further includes the step of providing a UV insertion tube assembly over a portion of an exterior of the insertion tube in order to protect the portion of the exterior of the insertion tube.

In a further embodiment of the first aspect of the present invention, the step of providing an UV insertion tube assembly further includes the steps of: providing an UV insertion tube having a first end and a second end such that the UV insertion tube is located over the portion of the exterior of the insertion tube; providing a boot connector operatively connected to the first end of the UV insertion tube; and providing an insertion tube distal tip connector operatively connected to the second end of the UV insertion tube.

In yet another embodiment of the first aspect of the present invention, the step of providing an ultraviolet (UV) light assembly further includes the step of providing a radiopaque marker that is located adjacent to the first end of the UV light source.

In a still another embodiment of the first aspect of the present invention, the step of providing a gastro-intestinal (GI) scope further includes the step of providing a sleeve assembly that is attached to the first end of the insertion tube.

In a yet further embodiment of the first aspect of the present invention, the sleeve assembly further includes a sleeve, a UV light operatively connected to an end of the sleeve, and a plurality of UV lights operatively connected to a circumference of the sleeve.

A second aspect of the present invention is a method of using a device for the eradication of clostridium difficile (C. Diff) in a patient's colon, including the steps of: providing a gastro-intestinal (GI) scope having an insertion tube having a first end and a second end, a control section such that the second end of the insertion tube is operatively connected to the control section, a universal cord having a first end and a second end such that the first end of the universal cord is operatively connected to the control section and the second end of the insertion tube is operatively connected to a suction connector; providing an ultraviolet (UV) light assembly, wherein the UV light assembly is further comprised of; a power source, a first electrical extension operatively connected to the power source, a UV light box operatively connected to the first electrical extension, and a UV light source operatively connected to the UV light box, wherein the UV light source includes a first end and a second end and wherein the UV light source is further comprised of a UV light having a tube and a plurality of UV lights located on the tube; inserting the insertion tube into a patient's colon such that the first end of the insertion tube is located adjacent to a cecum of the patient's colon; inserting the UV light source into the insertion tube until the first end of the UV light source is located adjacent to the first end of the insertion tube and the cecum of the patient's colon; removing the insertion tube; and activating the UV light source in order to eradicate clostridium difficile (C. Diff) located in a patient's colon.

In one embodiment of the second aspect of the present invention, the step of providing an ultraviolet (UV) light assembly further includes the step of providing UV light source extension such that the UV light source extension is operatively connected to the UV light box and the UV light source.

In another embodiment of the second aspect of the present invention, the method further includes the step of providing a UV insertion tube assembly over a portion of an exterior of the insertion tube in order to protect the portion of the exterior of the insertion tube.

In a further embodiment of the second aspect of the present invention, the step of providing an UV insertion tube assembly further includes the steps of: providing an UV insertion tube having a first end and a second end such that the UV insertion tube is located over the portion of the exterior of the insertion tube; providing a boot connector operatively connected to the first end of the UV insertion tube; and providing an insertion tube distal tip connector operatively connected to the second end of the UV insertion tube.

In yet another embodiment of the second aspect of the present invention, the step of providing an ultraviolet (UV) light assembly further includes the step of providing a radiopaque marker that is located adjacent to the first end of the UV light source.

In a still another embodiment of the second aspect of the present invention, the step of providing a gastro-intestinal (GI) scope further includes the step of providing a sleeve assembly that is attached to the first end of the insertion tube.

In a yet further embodiment of the second aspect of the present invention, the sleeve assembly further includes a sleeve, a UV light operatively connected to an end of the sleeve, and a plurality of UV lights operatively connected to a circumference of the sleeve.

A third aspect of the present invention is a method of using a gastro-intestinal (GI) scope for the eradication of clostridium difficile (C. Diff) in a patient's colon, including the steps of: providing a gastro-intestinal (GI) scope having an insertion tube having a first end and a second end, a control section such that the second end of the insertion tube is operatively connected to the control section, a universal cord having a first end and a second end such that the first end of the universal cord is operatively connected to the control section and the second end of the insertion tube is operatively connected to a suction connector providing a sleeve assembly that is attached to the first end of the insertion tube; providing an ultraviolet (UV) light assembly, wherein the UV light assembly is further comprised of; a power source, a first electrical extension operatively connected to the power source, a UV light box operatively connected to the first electrical extension, and a UV light source operatively connected to the UV light box, wherein the UV light source includes a first end and a second end and wherein the UV light source is further comprised of a UV light having a tube and a plurality of UV lights located on the tube; inserting the insertion tube into a patient's colon such that the first end of the insertion tube is located adjacent to a cecum of the patient's colon; inserting the UV light source into the insertion tube until the first end of the UV light source is located adjacent to the first end of the insertion tube and the cecum of the patient's colon; and removing the insertion tube and the UV light source from the patient's colon while simultaneously activating the UV light source in order to eradicate clostridium difficile (C. Diff) located in a patient's colon.

In one embodiment of the third aspect of the present invention, the step of providing an ultraviolet (UV) light assembly further includes the step of providing UV light source extension such that the UV light source extension is operatively connected to the UV light box and the UV light source.

In another embodiment of the third aspect of the present invention, the method further includes the step of providing a UV insertion tube assembly over a portion of an exterior of the insertion tube in order to protect the portion of the exterior of the insertion tube.

In a further embodiment of the third aspect of the present invention, the step of providing an UV insertion tube assembly further includes the steps of: providing an UV insertion tube having a first end and a second end such that the UV insertion tube is located over the portion of the exterior of the insertion tube; providing a boot connector operatively connected to the first end of the UV insertion tube; and providing an insertion tube distal tip connector operatively connected to the second end of the UV insertion tube.

In yet another embodiment of the third aspect of the present invention, the step of providing an ultraviolet (UV) light assembly further includes the step of providing a radiopaque marker that is located adjacent to the first end of the UV light source.

In a yet further embodiment of the third aspect of the present invention, the sleeve assembly further includes a sleeve, a UV light operatively connected to an end of the sleeve, and a plurality of UV lights operatively connected to a circumference of the sleeve.

The preferred programmable device which is used in conjunction with a gastro-intestinal (GI) scope during a colonoscopy by utilizing UV light to eradicate clostridium difficile (C. Diff) in infected patients, according to various embodiments of the present invention, offers the following advantages: ease of use; lightness in weight; durability; ease of disinfection of the interior of the colon; the ability to sterilize the interior of the colon; and compactness. In fact, in many of the preferred embodiments, these advantages are optimized to an extent that is considerably higher than heretofore achieved in prior, known gastro-intestinal (GI) scopes for use in the disinfection of colons.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 3 is a schematic illustration of a UV transparent insertion tube sleeve, constructed according the present invention;

FIG. 4 is a schematic illustration of a biopsy channel and suction connector plug cover, constructed according the present invention;

FIG. 7 is a schematic illustration of a second hanger for storing a gastro-intestinal (GI) scope that has been disinfected and sterilized, constructed according the present invention.

DETAILED DESCRIPTION OF THE PREFERRED EMBODIMENTS OF THE INVENTION

Figure 1:
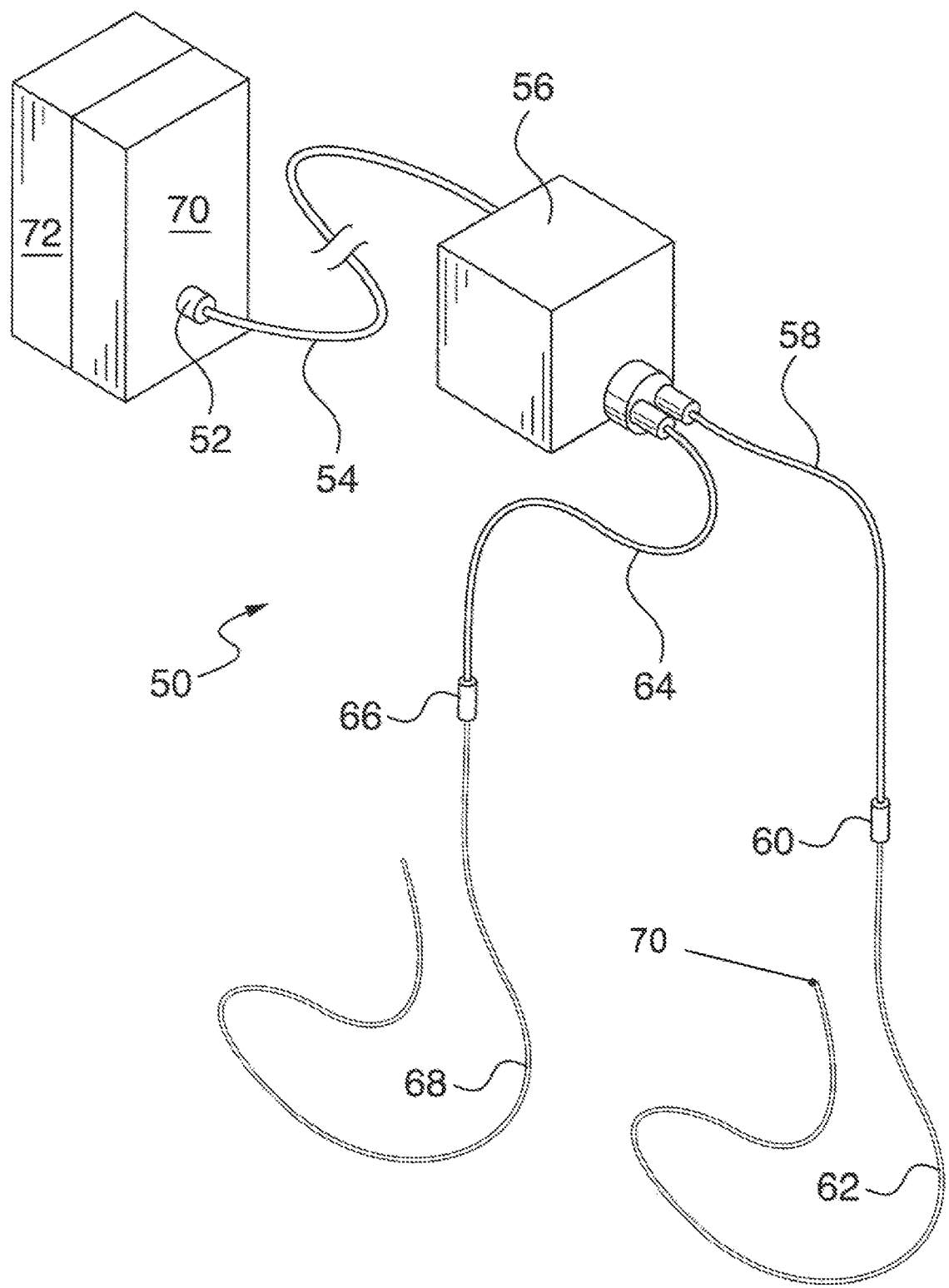
FIG. 1 is a schematic illustration of the ultra-violet (UV) light source assembly having a UV light source and a radiopaque marker, constructed according the present invention.

In order to address the shortcomings of the prior, known gastro-intestinal (GI) scope disinfection systems, reference is made now to FIGS. 1-7, where there is illustrated a programmable device 2 that can be used in conjunction with a gastro-intestinal (GI) scope 300, wherein the device 2 is capable of disinfecting and sterilizing the GI scope 300 by utilizing programmable ultraviolet (UV) light sources for the purposes of disinfecting and sterilizing the interior lumen of the gastro-intestinal (GI) scope 300 and a portion of the exterior of the scope. As will be explained hereinafter in greater detail, the programmable device 2 that can be used in conjunction with a gastro-intestinal (GI) scope 300 is capable of being programmed so as to disinfect/sterilize the gastro-intestinal (GI) scope 300 at desired times and/or dates. Also, the gastro-intestinal (GI) scope 300 can be stored for future use after the gastro-intestinal (GI) scope 300 has been disinfected/sterilized. Finally, the programmable device 2 that can be used in conjunction with a gastro-intestinal (GI) scope 300 is capable of disinfecting/sterilizing the interior of the gastro-intestinal (GI) scope 300 and a portion of the exterior of the gastro-intestinal (GI) scope 300.

As shown in FIG. 1-7, there is illustrated programmable device 2 that can be used in conjunction with a gastro-intestinal (GI) scope 300, wherein the device 2 is capable of disinfecting and sterilizing the GI scope 300 by utilizing programmable ultraviolet (UV) light sources for the purposes of disinfecting and sterilizing the interior and a portion of the exterior of the scope. Programmable device 2 includes, in part, ultraviolet (UV) light source assembly 50 (FIG. 1), UV light sources 62, 68 (FIGS. 2-4), UV insertion tube assembly 200 (FIG. 5), biopsy channel and suction connector plug cover assembly 250 (FIG. 6), conventional gastro-intestinal (GI) scope 300 (FIG. 7a), gastro-intestinal (GI) scope/UV light source assembly hanger assembly 350 (FIG. 8), gastro-intestinal (GI) scope storage assembly 400 (FIG. 9) and external UV light source assembly 450 (FIGS. 8 and 9).

Ultraviolet (UV) Light Source Assembly

With respect to ultraviolet (UV) light source assembly 50, as shown in FIG. 1, UV light source assembly 50 includes, in part, conventional electrical connector 52, conventional electrical extension 54, conventional UV light box 56, conventional fiber optic (UV light source) extension 58, conventional fiber optic connector 60, UV light source 62, conventional fiber optic (UV light source) extension 64, conventional fiber optic connector 66, UV light source 68, conventional power source 70 and conventional programmable timer 72. It is to be understood that conventional electrical connector 52 is used to connect UV light source assembly 50 to a conventional power source 70 such as an AC power source. Furthermore, it is to be understood that conventional fiber optic connector 60 and 66 are used to easily and quickly connect the UV light source 62 and the UV light source 68, respectively, to conventional fiber optic extension 58 and conventional fiber optic extension 64. However, it is to be further understood that the UV light source 62 and the UV light source 68 can be connected directly to the UV light box 56 and still perform in substantially the same manner. In any event, UV light source assembly 50 is used to provide UV light to the interior and a portion of the exterior of the gastro-intestinal (GI) scope 300 in order to disinfect/sterilize the interior and a portion of the exterior of the gastro-intestinal (GI) scope 300, as will be described in greater detail later. It is to be understood that conventional UV light box 56 can be equipped with a fan (not shown) so that the fan can be used to conventionally cool UV light source 62 and UV light source 68 and to keep the lumens of gastro-intestinal (GI) scope 300 dry.

UV Light Sources

Figure 2:
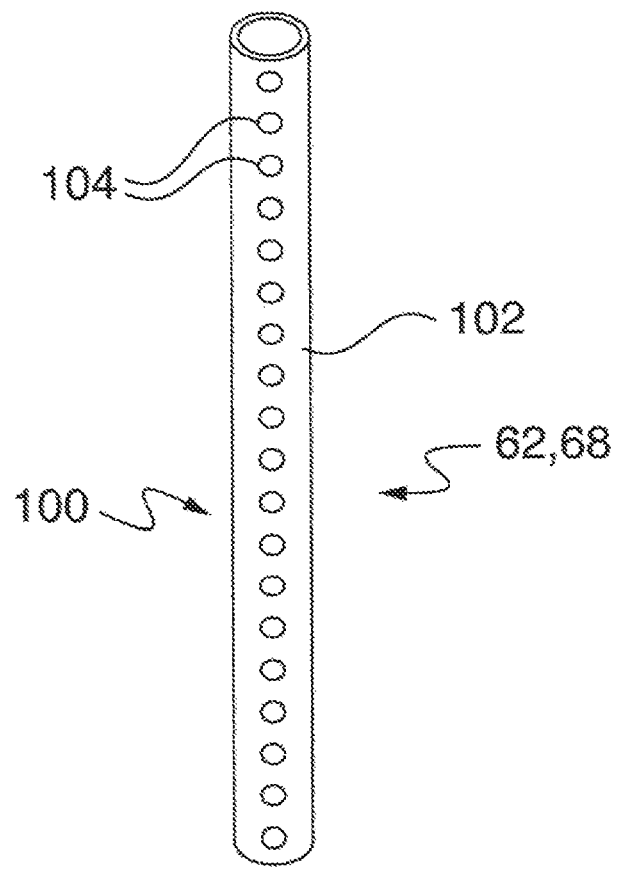
FIG. 2 is a schematic illustration of a UV light source, according the present invention.

Regarding UV light sources 62, 68, as shown in FIG. 2, UV light sources 62, 68 include, in part, UV light 100 having tube 102 and a plurality of UV lights 104 located on the tube 102 (FIG. 2). Preferably, tube 102 is constructed of any suitable, durable, flexible, UV resistant polymeric material. It is to be understood that UV lights 104 should be located on tube 102 so as to provide the maximum amount of UV light when the UV lights are activated.

UV Insertion Tube Assembly

Regarding UV insertion tube assembly 200, as shown in FIG. 3, UV insertion tube assembly 200 includes, in part, UV insertion tube 202, boot connector 204, boot clamp 206, insertion tube distal tip connector 208 and insertion tube distal tip clamps 210. Preferably, UV insertion tube 202, boot connector 204, boot clamp 206, insertion tube distal tip connector 208 and insertion tube distal tip clamps 210 are constructed of any suitable, durable, flexible, UV transparent material.

As will be described in greater detail later, another unique aspect of the present invention is the use of UV insertion tube assembly 200. In particular, after UV light source 62 has been placed within insertion tube 302 in order to subsequently disinfect/sterilize the interior of insertion tube 302, UV insertion tube assembly 200 is placed over insertion tube 302 so as to be able to subsequently disinfect/sterilize a portion of the exterior of insertion tube 302, as will be discussed in greater detail later.

Biopsy Channel and Suction Connector Plug Cover Assembly

With respect to biopsy channel and suction connector plug cover assembly 250, as shown in FIG. 4, biopsy channel and suction connector plug cover assembly 250 includes, in part, biopsy channel and suction connector plug cover 252. Preferably, biopsy channel and suction connector plug cover 252 is constructed of any suitable, durable, flexible, UV resistant polymeric material.

A further unique aspect of the present invention is biopsy channel and suction connector plug cover assembly 250. In particular, after UV light source 62 has been placed within insertion tube 302 (FIG. 5a) in order to subsequently disinfect/sterilize the interior of insertion tube 302 and UV light source 68 has been placed within universal cord 318 in order to subsequently disinfect/sterilize the interior of universal cord 318, biopsy channel and suction connector plug cover assemblies 250 are used to cover biopsy channel 308 and suction connector 320 (FIGS. 5a and 5b), respectively, as will be described in greater detail later. In this manner, the interiors of insertion tube 302 and universal cord 318 can be protected from having unwanted contaminants entering the interiors of insertion tube 302 and universal cord 318.

Gastro-Intestinal (GI) Scope

Figure 5A:
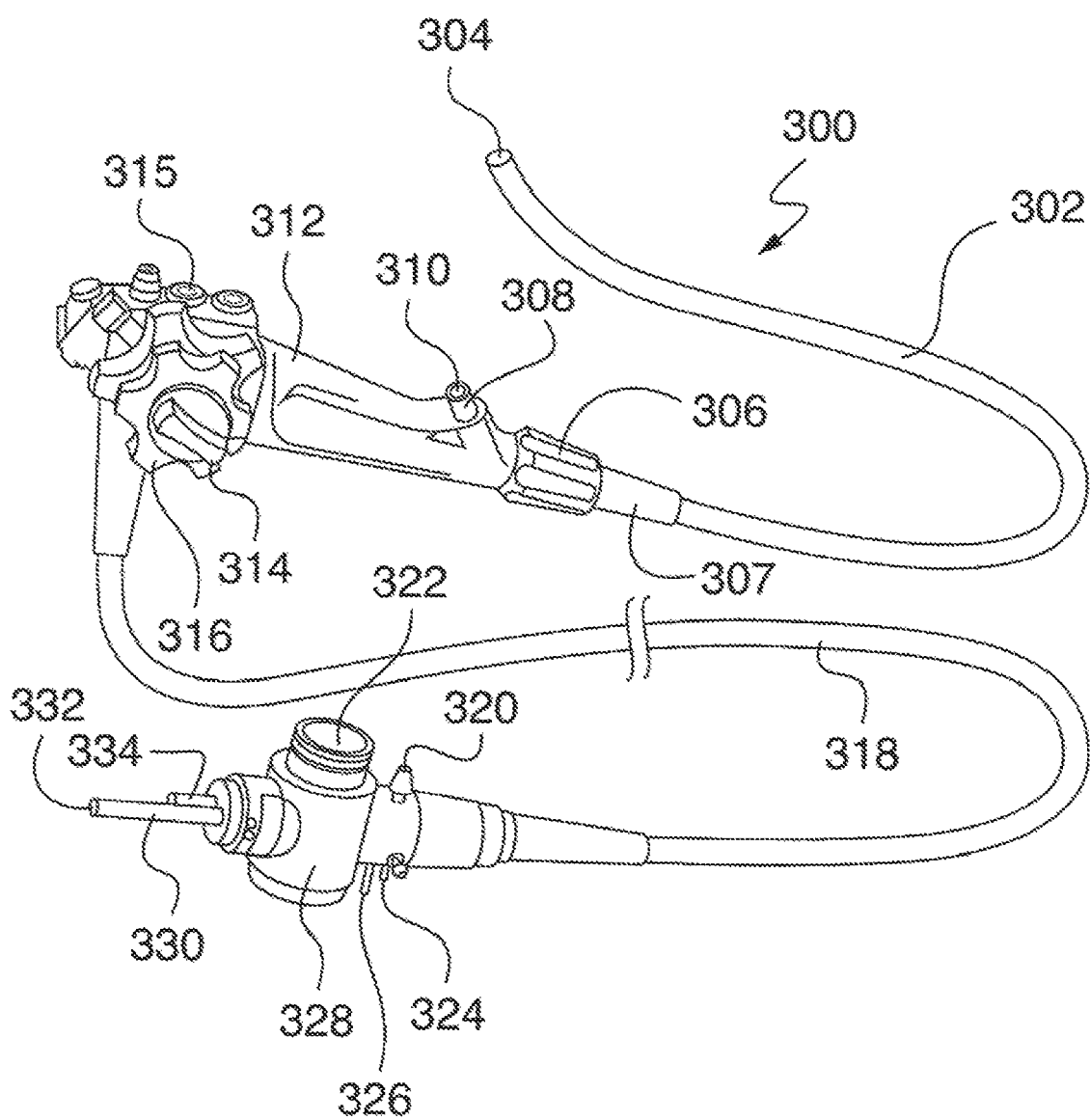
FIG. 5a is a schematic illustration of a conventional gastro-intestinal (GI) scope, according to the prior art.

Regarding conventional gastro-intestinal (GI) scope 300, as shown in FIG. 5a, conventional gastro-intestinal (GI) scope 300 includes, in part, insertion tube 302, distal tip 304, insertion tube stiffness control 306, boot 307, biopsy channel opening 308, biopsy valve 310, control section 312, right/left angulation lock 314, suction port channel 315, right/left angulation knob 316, universal cord 318, suction connector 320, video processor connection 322, air supply connector 324, water supply connector 326, light source connector 328, light guide 330, quartz lens 332, and air pipe 334.

Figure 5B:
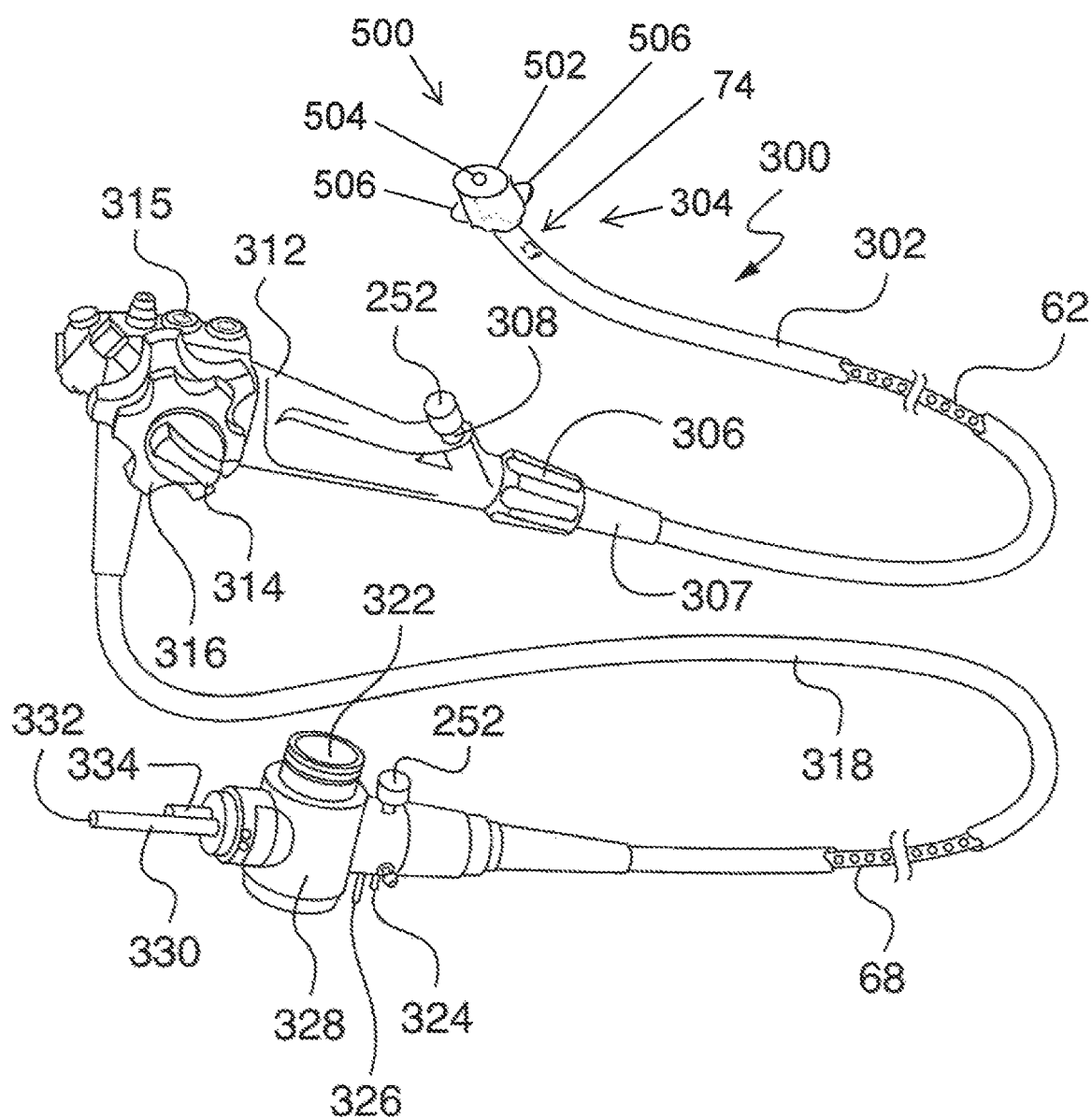
FIG. 5b is a schematic illustration of the gastro-intestinal (GI) scope with the UV light sources being located within the insertion tube and the universal cord and the covers attached and a sleeve assembly attached to the end of the insertion tube, constructed according to the present invention.

Another unique aspect of the present invention is the insertion of the UV light sources 62, 68 into the insertion tube 302 and the universal cord 318, respectively, of the conventional gastro-intestinal (GI) scope 300, as shown in FIG. 5b. As will be described in greater detail later, UV light source 62 is placed in insertion tube 302 by sliding UV light source 62 through distal tip 304 until UV light source 62 contacts biopsy channel opening 308. A biopsy channel and suction connector plug cover 252 is then placed over biopsy channel opening 308 (FIG. 5b) in order to protect the end of UV light source 62 that contacts biopsy channel opening 308. An insertion tube distal tip connector 208 and insertion tube distal tip clamps 210 (FIG. 3) are then used to protect the end of the UV light source 62 that is located near distal tip 304, as will be discussed in greater detail later. In this manner, the interior of insertion tube 302 which now includes UV light source 62 is substantially sealed so that contaminants cannot enter the interior of insertion tube 302 and/or contact UV light source 62. Similarly, UV light source 68 is placed in universal cord 318 by sliding UV light source 68 through suction port channel 315 until UV light source 68 contacts suction connector 320. A biopsy channel and suction connector plug cover 252 is then placed over suction connector 320 (FIG. 5b) in order to protect the end of UV light source 68 that contacts suction connector 320. UV light sources 62 and 68 are then conventionally connected to UV light source assembly 50 in order to activate UV light sources 62 and 68, as will be described in greater detail later.

Hanger Assemblies

Figure 6:
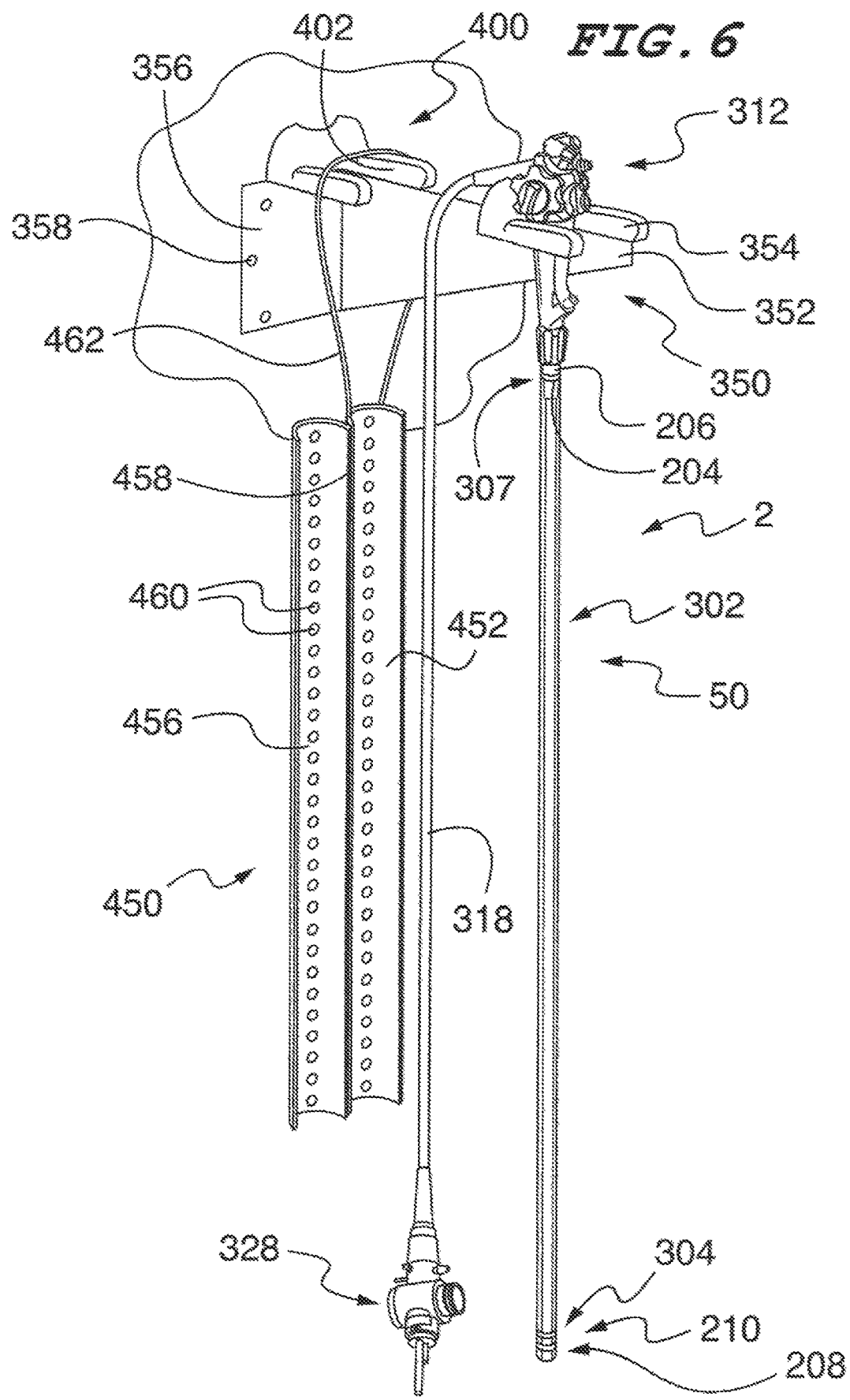
FIG. 6 is a schematic illustration of a first hanger for holding a programmable device that can be used in conjunction with a gastro-intestinal (GI) scope, wherein the device is capable of disinfecting and sterilizing the GI scope, constructed according the present invention.

With respect to hanger assembly 350 and storage assembly 400, as shown in FIGS. 6 and 7, gastro-intestinal (GI) scope/UV light source assembly hanger assembly 350 (FIG. 6) includes, in part, bracket 352, gastro-intestinal (GI) scope/UV light source assembly support 354, bracket extension 356 and fasteners 358. Preferably, bracket 352, bracket extension 356 and fasteners 358 are constructed of any suitable, durable, high strength material. It is to be understood that bracket extension 356 and fasteners 358 are used to firmly secure gastro-intestinal (GI) scope/UV light source assembly hanger assembly 350 and gastro-intestinal (GI) scope storage assembly 400 to a solid surface such as a wall, a door or other similar surface. A unique aspect of gastro-intestinal (GI) scope/UV light source assembly hanger assembly 350 is the use of gastro-intestinal (GI) scope/UV light source assembly support 354. In particular, gastro-intestinal (GI) scope/UV light source assembly support 354 is used to support programmable device 2 that can be used in conjunction with a gastro-intestinal (GI) scope 300 while programmable device 2 is used to disinfect/sterilize gastro-intestinal (GI) scope 300, as will be discussed in greater detail later.

With respect to gastro-intestinal (GI) scope storage assembly 400 (FIG. 7), gastro-intestinal (GI) scope storage assembly 400 includes, in part, gastro-intestinal (GI) scope/UV light source assembly support 402. It is to be understood that preferably gastro-intestinal (GI) scope storage assembly 400 and gastro-intestinal (GI) scope/UV light source assembly hanger assembly 350 are constructed to be substantially connected together or, at the least, located within a close proximity to each other. In this manner, once gastro-intestinal (GI) scope 300 has been installed with programmable device 2 on gastro-intestinal (GI) scope/UV light source assembly hanger assembly 350, gastro-intestinal (GI) scope 300 can then be quickly and easily moved to gastro-intestinal (GI) scope storage assembly 400 where the disinfected/sterilized gastro-intestinal (GI) scope 300 can be disinfected/sterilized with programmable device 2 and subsequently stored to future use, as will described in greater detail later.

External V Light Source Assembly

Regarding external UV light source assembly 450, as shown in FIGS. 6 and 7, external UV light source assembly 450 includes, in part, UV light source panels 452 and 456, panel hinge 458, conventional UV lights 460 and conventional external UV light source hanger 462. Preferably, UV light source panels 452 and 456, panel hinge 458, and external UV light source hanger 462 are constructed of any suitable, durable, high strength, UV resistant material. It is to be understood that panel hinge 458 is used to connect and allow UV light source panels 452 and 456 to hingedly open and close, as will be discussed in greater detail later. Also, it is to be understood that conventional UV lights 460 are located along the length of UV light source panels 452 and 456 and UV lights 460 are conventionally attached to the inside of UV light source panels 452 and 456 by fasteners, adhesives or the like. It is to be further understood that conventional external UV light source hanger 462 is shown as being a wire that holds the UV light source panels 452 and 456 on the gastro-intestinal (GI) scope/UV light source assembly support 402 of gastro-intestinal (GI) scope storage assembly 400. However, other suitable hangers can be used so long as the hanger is capable of adequately holding UV light source panels 452 and 456 on gastro-intestinal (GI) scope/UV light source assembly support 402 and allow UV light source panels 452 and 456 to easily open and close along hinge 456. Finally, it is to be understood that UV light source panels 452 and 456 are conventionally connected to programmable timer 72 so that the activation of UV light source panels 452 and 456 can be programmed in a manner that is similar to the programming of UV light source 62 and UV light source 68.

Construction of the Programmable Device that can be Used in Conjunction with a Gastro-Intestinal (GI) Scope In order to construct programmable device 2 that can be used in conjunction with a gastro-intestinal (GI) scope 300, attention is directed to FIGS. 1-7. As discussed earlier, UV light source 62 is placed in insertion tube 302 by sliding UV light source 62 through distal tip 304 until UV light source 62 contacts biopsy channel opening 308 (FIG. 5*b*). It is to be understood that the UV light source 62 can also be placed in insertion tube 302 by sliding UV light source 62 through biopsy channel opening 308 until UV light source 62 contacts distal tip 304. A biopsy channel and suction connector plug cover 252 is then placed over biopsy channel opening 308 (FIG. 7*b*) in order to protect the end of UV light source 62 that contacts biopsy channel opening 308. Similarly, UV light source 68 is placed in universal cord 318 by sliding UV light source 68 through suction port channel 315 until UV light source 68 contacts suction connector 320 (FIG. 5*b*). A biopsy channel and suction connector plug cover 252 is then placed over suction connector 320 (FIG. 5*b*) in order to protect the end of UV light source 68 that contacts suction connector 320. UV light sources 62 and 68 are then conventionally connected to UV light source assembly 50 in order to activate UV light sources 62 and 68, as previously discussed.

After UV light source 62 has been located within insertion tube 302 and UV light source 68 has been located within universal cord 318, UV insertion tube assembly 200 is placed over insertion tube 302 so as to be able to subsequently disinfect/sterilize a portion of the exterior of insertion tube 302. In particular, UV insertion tube assembly 200 is placed over insertion tube 302 so that boot connector 204 (FIG. 3) contacts boot 307 (FIG. 5*b*). Boot clamp 206 is then used to secure boot connector 204 to boot 307 (FIG. 6). Insertion tube distal tip connector 208 is located adjacent to distal tip 304 and the end of UV light source 62 that is located adjacent to distal tip 304. Distal tip clamps 210 are then used to secure insertion tube distal tip connector 208 to distal tip 304 and the end of UV light source 62. The UV light source assembly 50 can then be conventionally connected to the end of UV light source 62 that extends out of distal tip 304 and insertion tube distal tip connector 208 in order to activate UV light source 62.

Operation of the Programmable Device 2 that can be Used in Conjunction with a Gastro-Intestinal (GI) Scope Once UV light source 62 has been located within insertion tube 302, UV light source 68 has been located within universal cord 318, and UV insertion tube assembly 200 is placed over insertion tube 302, the programmable device 2 is then placed on gastro-intestinal (GI) scope/UV light source assembly hanger assembly 350 such that control section 312 is supported by gastro-intestinal (GI) scope/UV light source assembly support 354. It is to be understood that UV insertion tube assembly 200 can be placed over insertion tube 302 after programmable device 2 has been placed on gastro-intestinal (GI) scope/UV light source assembly hanger assembly 350.

In order to sterilize/disinfect gastro-intestinal (GI) scope 300, gastro-intestinal (GI) scope 300 which now includes UV light source 62 that has been located within insertion tube 302, UV light source 68 that has been located within universal cord 318 and UV insertion tube assembly 200 that is placed over insertion tube 302 is moved to gastro-intestinal (GI) scope storage assembly 400 (FIG. 7). As discussed above, UV light source panels 452 and 456 are rotated around panel hinge 458 so that UV light source panels 452 and 456 substantially surround the area where UV insertion tube assembly 200 is placed over insertion tube 302. Finally, UV light source 62 and UV light source 68 are connected to UV light box 56 and UV light source panels 452 and 456 are connected to programmable timer 72, as previously discussed.

Once the UV light source panels 452 and 456 have been located around the area where UV insertion tube assembly 200 is placed over insertion tube 302 and connected to programmable timer 72 and UV light source 62 and UV light source 68 have been connected to UV light box 56 (and then programmable timer 72), the end user can use programmable timer 72 (FIG. 1) to program the amount of time that UV light source panels 452 and 456 and UV light sources 62 and 68 can be activated in order to sterilize and disinfect gastro-intestinal (GI) scope 300. For example, if the UV light source panels 452 and 456 and UV light sources 62 and 68 are activated for a predetermined amount of time and/or for a predetermined amount of UV exposure, this exposure time has been shown to adequately disinfect the interior of the insertion tube 302 and universal cord 318 and a portion of the exterior of insertion tube 302. However, if it is desired to also sanitize the interior of the insertion tube 302 and universal cord 318 and a portion of the exterior of insertion tube 302, the UV light source panels 452 and 456 and UV light sources 62 and 68 can be activated for a longer amount of time and/or for a longer predetermined amount of UV exposure. In particular, the time it takes for complete sterilization could take up to 30 minutes. Also, the closer the UV light is to gastro-intestinal (GI) scope 300, the faster it sterilizes gastro-intestinal (GI) scope 300 with the known factor being that the intensity of the light plays a big role in the ability to sterilize the gastro-intestinal (GI) scope 300.

A still another unique aspect of the present invention is that programmable timer 72 can also be programmed to activate the UV light source panels 452 and 456 and UV light sources 62 and 68 at any desired time and for any desired activation period. For example, the conventional timing device 72 can be connected to the programmable device 2 in order that the programmable device 2 can be turned off/turned on at a desired date and/or for a desired time. In particular, if the gastro-intestinal (GI) scope 300 has been previously disinfected/sanitized but a predetermined period of time has elapsed since the gastro-intestinal (GI) scope 300 was disinfected/sanitized, the programmable timer 72 can also be programmed to re-activate the UV light source panels 452 and 456 and UV light sources 62 and 68 at any desired time interval and for any desired activation period. Furthermore, the end user can program programmable device 2 so as to activate the UV light source panels 452 and 456 and UV light sources 62 and 68 at a later time.

It is to be understood that while the present invention has been described for disinfecting/sterilizing a gastro-intestinal (GI) scope, the present invention could also be used to disinfect/sterilize cystoscopes and instruments, ureteroscopes and instruments, bronchoscopes, arterial lines and central lines, and other medical devices not able to be sterilized traditionally with steam due to their fragile design. Furthermore, disinfecting/sterilizing with the present invention would not leave any chemical residue that can possibly harm the patient.

Operation of the Programmable Device 2 that can be Used in Conjunction with a Gastro-Intestinal (GI) Scope in Order to Eradicate the Clostridium Difficile (C. Diff) in a Patient's Colon After the gastro-intestinal (GI) scope 300 was disinfected/sanitized and stored, as discussed above, the UV light source 62 can remain in the gastro-intestinal (GI) scope 300 with the UV insertion tube assembly 200 protecting the insertion tube 302 while the following new and improved endoscopy procedure is commenced. A unique aspect of the present invention is that once the surgeon starts the endoscopy procedure, the UV insertion tube assembly 200 can be used as a sterile barrier between the surgeon's gloves and the insertion tube 302. This allows insertion tube 302 to remain sterile prior to advancing the gastro-intestinal (GI) scope 300 further into the patient's colon.

Another unique aspect of the present invention is the use of sleeve assembly 500 as shown in FIG. 5B. As shown in FIG. 5B, the sleeve assembly 500 is conventionally located over the distal end of insertion tube 302. Sleeve assembly 500 includes, in part, a sleeve 502, a UV light 504 located on the end of sleeve 502, and a plurality of UV lights 506 located around a circumference of the sleeve 502. Preferably, sleeve 502 is constructed of the same material as insertion tube 302. It is to be understood that UV light 504 and UV lights 506 are conventionally attached to sleeve 502. In this manner, UV light 504 and UV lights 506 along with UV light source 62 can be used to provide substantially 360 degrees of UV light on the colon wall. It is to be understood that sleeve assembly 500 may have conventional power wires (not shown) located within the insertion tube 302 to conventionally connect the UV lights 504 and 506 to conventional power source 70 and conventional programmable timer 72 that will activate the UV lights 304 and 306 on the sleeve assembly 500 at the distal end of insertion tube 302.

With respect to the new and improved endoscopy procedure, initially, insertion tube 302 will be inserted into the patient's colon until the end of the insertion tube 302 has reached the end of the patient's colon which is commonly known as the cecum. The UV light source 62 is then located within the insertion tube 302, as discussed above. It is to be understood that a conventional radiopaque marker 74 can be conventionally located near the end of UV light source 62 (FIGS. 1 and 5B). In this manner, the radiopaque marker 74 can initially be located adjacent to the cecum prior to the beginning of the eradication of the Clostridium Difficile (C. Diff) in the patient's colon.

In one embodiment of the present invention, the surgeon will then simultaneously activate the UV light source 62 and UV lights 504 and 506, as discussed above, and slowly pull the insertion tube 302 out of the patient with a predetermined UV light range of 220-300 nm to ensure that the UV lights 504 and 506 and UV light source 62 will eradicate the C. Diff throughout the desired length of the patient's colon. In this manner, the UV light will be bacteriocidal with respect to the Clostridium Difficile (C. Diff). It is to be understood that the amount of time that the UV light source 62 and UV lights 504 and 506 are activated can be adjusted using programmable device 2.

In another embodiment of the present invention, as discussed above, the UV light source 62 is inserted into the insertion tube 302 after the insertion tube 302 has been inserted into the patient's colon. It is to be understood that in this embodiment, the sleeve assembly 500 is not attached to the end of insertion tube 302. In this manner, the insertion tube 302 is pulled out of the patient's colon and the UV light source 62 remains behind in the patient's colon. In this embodiment, the radiopaque marker 74 is then conventionally used to show the position of the end of the UV light source 62 within the colon of the patient using conventional X-ray techniques after the insertion tube 302 has been completely removed from the patient.

After the insertion tube 302 has been removed, the surgeon will then activate the UV light in the UV light source 62, as discussed above, with a predetermined UV light range of 220-300 nm to ensure that the UV light source 62 will eradicate the C. Diff throughout the length of the patient's colon that is in contact with the UV light source 62. As discussed above, the amount of time that the UV light source 62 is activated can be adjusted using programmable device 2.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein is a new and improved programmable device that can be used in conjunction with a gastro-intestinal (GI) scope during a colonoscopy to provide UV light to eradicate clostridium difficile (C. Diff) in infected patients, according to various embodiments of the present invention, offers the following advantages: ease of use; lightness in weight; durability; ease of disinfection of the interior of the colon; the ability to sterilize the interior of the colon; and compactness. In fact, in many of the preferred embodiments, these advantages of ease of use, lightness in weight, durability, ease of disinfection of the interior of the colon, the ability to sterilize the interior of the colon, and compactness are optimized to an extent that is considerably higher than heretofore achieved in prior, known gastro-intestinal (GI) scopes for use in the disinfection of colons.

I claim:

1. A method of using a gastro-intestinal (GI) scope for the eradication of clostridium difficile (C. Diff) in a patient's colon, comprising the steps of:
   providing a gastro-intestinal (GI) scope having an insertion tube having a first end and a second end, wherein the insertion tube is constructed of an ultraviolet (UV) light transparent material, a control section such that the second end of the insertion tube is operatively connected to the control section, a universal cord having a first end and a second end such that the first end of the universal cord is operatively connected to the control section and the second end of the insertion tube is operatively connected to a suction connector;
   providing an ultraviolet (UV) light assembly, wherein the UV light assembly is further comprised of;
      a power source,
      a first electrical extension operatively connected to the power source,
      a UV light box operatively connected to the first electrical extension,
      a UV light source operatively connected to the UV light box, wherein the UV light source includes a first end and a second end and wherein the UV light source is further comprised of a UV light having a tube and a plurality of UV lights located on the tube, and a radiopaque marker that is located near the first end of the UV light source in order for the radiopaque marker to initially be located adjacent to a patient's cecum prior to a beginning of an eradication of the of clostridium difficile (C. Diff) in a patient's colon;

inserting the insertion tube into a patient's colon such that the first end of the insertion tube is located adjacent to the cecum of the patient's colon;

inserting the UV light source into the insertion tube until the first end of the UV light source is located adjacent to the first end of the insertion tube and the radiopaque marker is located adjacent to the cecum of the patient's colon;

removing the insertion tube from the patient's colon; and upon removal of the insertion tube from the patient's colon, removing the UV light source from the patient's colon while simultaneously activating the UV light source in order to eradicate clostridium difficile (C. Diff) located in a patient's colon.

2. The method of using a gastro-intestinal (GI) scope for the eradication of clostridium difficile (C. Diff) in a patient's colon, according to claim 1, wherein the step of providing an ultraviolet (UV) light assembly is further comprised of the step of:

providing UV light source extension such that the UV light source extension is operatively connected to the UV light box and the UV light source.

3. The method of using a gastro-intestinal (GI) scope for the eradication of clostridium difficile (C. Diff) in a patient's colon, according to claim 1, wherein the method is further comprised of the step of:

providing a UV insertion tube assembly over a portion of an exterior of the insertion tube in order to protect the portion of the exterior of the insertion tube.

4. The method of using a gastro-intestinal (GI) scope for the eradication of clostridium difficile (C. Diff) in a patient's colon, according to claim 3, wherein the step of providing an UV insertion tube assembly is further comprised of the steps of:

providing an UV insertion tube having a first end and a second end such that the UV insertion tube is located over the portion of the exterior of the insertion tube;

providing a boot connector operatively connected to the first end of the UV insertion tube; and providing an insertion tube distal tip connector operatively connected to the second end of the UV insertion tube.

5. The method of using a gastro-intestinal (GI) scope for the eradication of clostridium difficile (C. Diff) in a patient's colon, according to claim 1, wherein the step of providing a gastro-intestinal (GI) scope is further comprised of the step of:

providing a sleeve assembly that is attached to the first end of the insertion tube.

6. The method of using a gastro-intestinal (GI) scope for the eradication of clostridium difficile (C. Diff) in a patient's colon, according to claim 5, wherein the sleeve assembly is further comprised of:

a sleeve;

a UV light operatively connected to an end of the sleeve; and a plurality of UV lights operatively connected to a circumference of the sleeve.

7. A method of using a device for the eradication of clostridium difficile (C. Diff) in a patient's colon, comprising the steps of:

providing a gastro-intestinal (GI) scope having an insertion tube having a first end and a second end, wherein the insertion tube is constructed of an ultraviolet (UV) light transparent material, a control section such that the second end of the insertion tube is operatively connected to the control section, a universal cord having a first end and a second end such that the first end of the universal cord is operatively connected to the control section and the second end of the insertion tube is operatively connected to a suction connector;

providing an ultraviolet (UV) light assembly, wherein the UV light assembly is further comprised of;

a power source, a first electrical extension operatively connected to the power source, a UV light box operatively connected to the first electrical extension, a UV light source operatively connected to the UV light box, wherein the UV light source includes a first end and a second end and wherein the UV light source is further comprised of a UV light having a tube and a plurality of UV lights located on the tube, and a radiopaque marker that is located near the first end of the UV light source in order for the radiopaque marker to initially be located adjacent to a patient's cecum prior to a beginning of an eradication of the of clostridium difficile (C. Diff) in a patient's colon;

inserting the insertion tube into a patient's colon such that the first end of the insertion tube is located adjacent to the cecum of the patient's colon;

inserting the UV light source into the insertion tube until the first end of the UV light source is located adjacent to the first end of the insertion tube and the radiopaque marker is located adjacent to the cecum of the patient's colon;

removing the insertion tube; and removing the UV light source while simultaneously activating the UV light source in order to eradicate clostridium difficile (C. Diff) located in a patient's colon.

8. The method of using a device for the eradication of clostridium difficile (C. Diff) in a patient's colon, according to claim 7, wherein the step of providing an ultraviolet (UV) light assembly is further comprised of the step of:

providing UV light source extension such that the UV light source extension is operatively connected to the UV light box and the UV light source.

9. The method of using a device for the eradication of clostridium difficile (C. Diff) in a patient's colon, according to claim 7, wherein the method is further comprised of the step of:

providing a UV insertion tube assembly over a portion of an exterior of the insertion tube in order to protect the portion of the exterior of the insertion tube.

10. The method of using a device for the eradication of clostridium difficile (C. Diff) in a patient's colon, according to claim 9, wherein the step of providing an UV insertion tube assembly is further comprised of the steps of:

providing an UV insertion tube having a first end and a second end such that the UV insertion tube is located over the portion of the exterior of the insertion tube;

providing a boot connector operatively connected to the first end of the UV insertion tube; and providing an insertion tube distal tip connector operatively connected to the second end of the UV insertion tube.

11. The method of using a device for the eradication of clostridium difficile (C. Diff) in a patient's colon, according to claim 7, wherein the step of providing a gastro-intestinal (GI) scope is further comprised of the step of:

providing a sleeve assembly that is attached to the first end of the insertion tube.

12. The method of using a device for the eradication of clostridium difficile (C. Diff) in a patient's colon, according to claim 11, wherein the sleeve assembly is further comprised of:

a sleeve;

a UV light operatively connected to an end of the sleeve; and a plurality of UV lights operatively connected to a circumference of the sleeve.

13. A method of using a gastro-intestinal (GI) scope for the eradication of clostridium difficile (C. Diff) in a patient's colon, comprising the steps of:

providing a gastro-intestinal (GI) scope having an insertion tube having a first end and a second end, wherein the insertion tube is constructed of an ultraviolet (UV) light transparent material, a control section such that the second end of the insertion tube is operatively connected to the control section, a universal cord having a first end and a second end such that the first end of the universal cord is operatively connected to the control section and the second end of the insertion tube is operatively connected to a suction connector;

providing a sleeve assembly that is attached to the first end of the insertion tube and providing an ultraviolet (UV) light assembly, wherein the UV light assembly is further comprised of;

a power source, a first electrical extension operatively connected to the power source, a UV light box operatively connected to the first electrical extension, a UV light source operatively connected to the UV light box, wherein the UV light source includes a first end and a second end and wherein the UV light source is further comprised of a UV light having a tube and a plurality of UV lights located on the tube, and a radiopaque marker that is located near the first end of the UV light source in order for the radiopaque marker to initially be located adjacent to a patient's cecum prior to a beginning of an eradication of the of clostridium difficile (C. Diff) in a patient's colon;

inserting the insertion tube into a patient's colon such that the first end of the insertion tube is located adjacent to the cecum of the patient's colon;

inserting the UV light source into the insertion tube until the first end of the UV light source is located adjacent to the first end of the insertion tube and the radiopaque marker is located adjacent to the cecum of the patient's colon;

removing the insertion tube from the patient's colon; and upon removal of the insertion tube from the patient's colon, removing the UV light source from the patient's colon while simultaneously activating the UV light source in order to eradicate clostridium difficile (C. Diff) located in a patients colon.

14. The method of using a gastro-intestinal (GI) scope for the eradication of clostridium difficile (C. Diff) in a patient's colon, according to claim 13, wherein the step of providing an ultraviolet (UV) light assembly is further comprised of the step of:

providing UV light source extension such that the UV light source extension is operatively connected to the UV light box and the UV light source.

15. The method of using a gastro-intestinal (GI) scope for the eradication of clostridium difficile (C. Diff) in a patients colon, according to claim 13, wherein the method is further comprised of the step of:

providing a UV insertion tube assembly over a portion of an exterior of the insertion tube in order to protect the portion of the exterior of the insertion tube.

16. The method of using a gastro-intestinal (GI) scope for the eradication of clostridium difficile (C. Diff) in a patient's colon, according to claim 15, wherein the step of providing an UV insertion tube assembly is further comprised of the steps of:

providing an UV insertion tube having a first end and a second end such that the UV insertion tube is located over the portion of the exterior of the insertion tube;

providing a boot connector operatively connected to the first end of the UV insertion tube; and providing an insertion tube distal tip connector operatively connected to the second end of the UV insertion tube.

17. The method of using a gastro-intestinal (GI) scope for the eradication of clostridium difficile (C. Diff) in a patient's colon, according to claim 13, wherein the sleeve assembly is further comprised of:

a sleeve;

a UV light operatively connected to an end of the sleeve; and a plurality of UV lights operatively connected to a circumference of the sleeve.

* * * * *